United States Patent
Schmid et al.

(10) Patent No.: US 7,241,875 B2
(45) Date of Patent: Jul. 10, 2007

(54) METHOD FOR THE PRODUCTION OF SURFACE ACTIVE AGENT MIXTURES

(75) Inventors: Karl Heinz Schmid, Mettmann (DE); Almud Folge, Langenfeld (DE); Ansgar Behler, Bottrop (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 44 days.

(21) Appl. No.: 10/476,593

(22) PCT Filed: Apr. 27, 2002

(86) PCT No.: PCT/EP02/04694

§ 371 (c)(1), (2), (4) Date: Oct. 31, 2003

(87) PCT Pub. No.: WO02/090369

PCT Pub. Date: Nov. 14, 2002

(65) Prior Publication Data

US 2004/0136939 A1 Jul. 15, 2004

(30) Foreign Application Priority Data

May 8, 2001 (DE) .............................. 101 22 255

(51) Int. Cl.
- *C07H 15/00* (2006.01)
- *C07H 1/00* (2006.01)
- *A61K 31/70* (2006.01)

(52) U.S. Cl. ...................... 536/18.5; 536/4.1; 536/124; 514/25

(58) Field of Classification Search ................. 536/4.1, 536/18.5, 124; 514/25
See application file for complete search history.

(56) References Cited

U.S. PATENT DOCUMENTS

| | | | |
|---|---|---|---|
| 4,599,188 A | 7/1986 | Llenado | |
| 4,806,275 A | 2/1989 | Johnson et al. | |
| 5,179,201 A | 1/1993 | Oftring et al. | |
| 5,773,595 A * | 6/1998 | Weuthen et al. | 536/17.9 |
| 5,908,928 A | 6/1999 | Milstein et al. | |
| 5,925,747 A * | 7/1999 | Uphues et al. | 536/18.5 |

FOREIGN PATENT DOCUMENTS

| | | |
|---|---|---|
| WO | WO 97/42299 | 11/1997 |
| WO | WO 99/24538 | 5/1999 |

OTHER PUBLICATIONS

Biermann, et al., "Alkylpolyglucoside—Technologie und Eigenschaften", Starch/Stärke, vol. 45, VCH Verlagsgesellschaft mbH, Weinheim, (1993), pp. 281-288.

Salka, "Alkyl Polyglycosides Properties and Applications", Cosmetics & Toiletries, vol. 108, (Mar. 1993), pp. 89-94.

Kahre, et al, "Alkylpolyglycoside—Ein neues Konzept für Pflege und Verträglichkeit in der Kosmetik", SÖFW-Journal, vol. 121, No. 8, (1995), pp. 598, 600-601, 604-611.

J. March, Advanced Organic Chemistry, Third Edition, John Wiley & Sons, (1985), pp. 342, 346.

* cited by examiner

*Primary Examiner*—Shaojia Anna Jiang
*Assistant Examiner*—Everett White
(74) *Attorney, Agent, or Firm*—John F. Daniels; Jane E. Alexander

(57) ABSTRACT

An aqueous surfactant mixture comprised of an alkyl and/or alkenyl oligoglycoside ether carboxylic acid is made by a process comprising reacting in an aqueous solution an alkyl and/or alkenyl oligoglycoside and an ω-halocarboxylic acid or a salt or ester thereof in the presence of alkali.

11 Claims, No Drawings

METHOD FOR THE PRODUCTION OF SURFACE ACTIVE AGENT MIXTURES

BACKGROUND OF THE INVENTION

This invention relates to a process for the production of surfactant mixtures containing alkyl and/or alkenyl oligoglycoside ether carboxylic acids by reaction of an aqueous solution of alkyl and/or alkenyl oligoglycosides with ω-halocarboxylic acids, salts or esters thereof in the presence of alkali.

PRIOR ART

It is known that alkyl and/or alkenyl oligoglycoside ether carboxylic acids can be produced by reaction of alkyl and/or alkenyl oligoglycosides with halocarboxylic acids in alkaline medium. Since alkyl and/or alkenyl oligoglycosides in their molten state have very high viscosities, suitable solvents have to be added during the reaction to avoid hydrolysis of the halocarboxylic acids or salts or esters thereof. International patent application WO 97/42299 describes the reaction with toluene as solvent. In this case, an aqueous solution of alkyl and/or alkenyl oligoglycosides is first freed from water using toluene as entraining agent in order to prevent hydrolysis of the sodium chloroacetate used, after which the carboxylation reaction is carried out in toluene.

Now, the problem addressed by the present invention was to provide a more simple and inexpensive process for the production of alkyl and/or alkenyl oligoglycoside ether carboxylic acids in which the removal of water from the alkyl and/or alkenyl oligoglucoside solution would no longer be necessary and the reaction with ω-halocarboxylic acids, salts or esters thereof to form alkyl and/or alkenyl oligoglycoside ether carboxylic acids could be carried out with high yields in the absence of organic solvents.

DESCRIPTION OF THE INVENTION

The present invention relates to a process for the production of surfactant mixtures containing alkyl and/or alkenyl oligoglycoside ether carboxylic acids, characterized in that an aqueous solution of at least one alkyl and/or alkenyl oligoglycoside is reacted with a ω-halocarboxylic or a salt or ester thereof in the presence of alkali.

It has surprisingly been found that alkyl and/or alkenyl oligoglycoside ether carboxylic acids can be produced in high yields by reaction of an aqueous solution of alkyl and/or alkenyl oligoglycosides with ω-halocarboxylic acids, salts or esters thereof and alkali without any need for the removal of water. By comparison with the prior art, this process is not only more environmentally friendly through the avoidance of organic solvents, it is also less expensive and easier to carry out. It is of particular advantage that the surfactant mixtures thus obtained can be directly used in cosmetic formulations without any need for the expensive removal of organic solvents.

Alkyl and/or Alkenyl Oligoglycosides

The surfactant mixtures according to the invention are produced using alkyl and alkenyl oligoglycosides corresponding to formula (I):

$$R^1O\text{-}[G]_p \qquad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The synoptic articles by Biermann et al. in Starch/Stärke 45, 281 (1993), B. Salka in Cosm. Toil. 108, 89 (1993) and J. Kahre et al. in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl group $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8\text{-}18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^1$ may also be derived from primary alcohols containing 12 to 22, preferably 12 to 18 and more particularly 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Alkylating Agents

ω-Halocarboxylic acids, salts or esters thereof are used for the production of the surfactant mixtures according to the invention. According to the invention, suitable ω-halocarboxylic acids, salts or esters thereof are any such compounds known from the literature. Potassium or sodium monochloroacetate (MCA) is preferably used.

Process

To produce the surfactant mixtures according to the invention, an aqueous solution of alkyl and/or alkenyl oligoglycosides, preferably $C_{2/14}$ alkyl polyglucosides, is introduced into a stirred vessel. This aqueous solution contains at most 70, preferably 20 to 65 and more particularly 50 to 60% by weight of alkyl and/or alkenyl oligoglycosides, based on the active substance content. The solution is then heated under nitrogen to 50 to 100° C., preferably 60 to 85° C. and more particularly to 80° C., after which alkali is added. The term "alkali" in the context of the invention is understood to encompass solid alkali metal hydroxides or alkali metal carbonates or alkali metal hydroxide dissolved in water, preferably sodium hydroxide or alkali metal carbonate. Solid alkali metal hydroxide, more particularly sodium hydroxide, for example in the form of NaOH prills, is preferably used.

After stirring for 1 to 4 hours and preferably 1 hour (slight increase in temperature to 90° C.), the ω-halocarboxylic acid, a salt or ester thereof, preferably sodium chloroacetate (MCA), is added and the mixture is stirred at 50 to 100° C. and preferably at 80° C. until the ω-halocarboxylic acid used has been completely reacted. The reaction is monitored on the basis of the quantity of alkali metal halide, preferably sodium chloride, released. In one particular embodiment of the invention, the alkyl and/or alkenyl oligoglycoside is reacted with the ω-halocarboxylic acid, salt or ester, preferably sodium monochloroacetate (MCA), in a molar ratio of 1:0.5 to 1:3.5 and preferably in a molar ratio of 1:1 to 1:2. In another embodiment of the invention, the molar ratio of alkali to ω-halocarboxylic acid, salt or ester is 1:0.5 to 1:1.5 and preferably 1:1 to 1:1.3. The reaction is carried out in the absence of organic solvents.

After a reaction time of 2 to 8, preferably 3 to 6 and more particularly 3 to 5 hours, alkyl and/or alkenyl oligoglycoside ether carboxylic acids are obtained in a yield of 30 to 100%, based on the quantity of alkyl and/or alkenyl oligoglycosides used.

The surfactant mixtures produced in accordance with the invention preferably contain 50 to 70% by weight and more particularly 10 to 45% by weight of alkyl and/or alkenyl oligoglycoside ether carboxylic acids and 0 to 50% by weight and more particularly 5 to 30% by weight of unreacted alkyl and/or alkenyl oligoglycoside. The balance to 100% by weight of the surfactant mixture is preferably made up of alkali metal halide formed, carboxylic acid released from the halocarboxylic acid and water.

If desired, water may be subsequently removed by conventional drying processes, preferably freeze drying, so that a dry powder of the surfactant mixture produced in accordance with the invention with a residual water content of at most 5% by weight, preferably at most 3% by weight and more particularly at most 1% by weight, based on the dried surfactant mixture, is obtained.

Commercial Applications

The surfactant mixtures according to the invention may be adjusted to any concentration by addition of water. The water content may be from 20 to 90% by weight and is preferably in the range from 30 to 80% by weight and more particularly in the range from 40 to 70% by weight.

The surfactant mixture according to the invention may be used in surface-active preparations such as, for example, laundry and dishwashing detergents, household cleaners and cosmetic and/or pharmaceutical preparations. These surface-active preparations may contain pearlizing waxes, consistency factors, thickeners, superfatting agents, stabilizers, silicone compounds, fats, waxes, lecithins, phospholipids, antioxidants, deodorants, antiperspirants, antidandruff agents, swelling agents, tyrosine inhibitors, hydrotropes, solubilizers, preservatives, perfume oils, dyes, other surfactants and the like as further auxiliaries and additives. Cosmetic and/or pharmaceutical preparations in the context of the invention are, for example, oral hygiene and dental care preparations, hair shampoos, hair lotions, foam baths, shower baths, creams, gels, lotions, alcoholic and aqueous/alcoholic solutions and emulsions.

EXAMPLES

Example 1

Preparation of Surfactant Mixture 1

24.41 kg (0.029 kmol) of Plantacare 1200 UP ($C_{12/14}$ alkyl polyglucoside) containing 50% by weight $C_{12/14}$ alkyl polyglucoside were introduced into a stirred vessel and heated under nitrogen to 80° C. After reaching the temperature, 1.51 kg (0.0377 kmol) of NaOH prills were added and the mixture was stirred for one hour, its temperature increasing slightly to 90° C. 4.39 kg (0.0377 kmol) of sodium chloroacetate (MCA) were then added and the mixture was stirred at 80° C. until the MCA used had been completely reacted. The reaction was monitored through the quantity of NaCl released. After a reaction time of 4.5 hours, the reaction was terminated. A viscous, light yellow liquid with the following composition was obtained:

| | |
|---|---|
| free, unreacted APG: | 15.3% |
| NaCl: | 4.3% |
| glycolic acid: | 2.8% |
| Dry residue: | 51.7% |
| $C_{12/14}$ alkyl polyglucoside ethyl carboxylate: | 29.3% |

Example 2

Preparation of Surfactant Mixture 2

673.3 g (0.8 mol) of Plantacare 1200 UP ($C_{12/14}$ alkyl polyglucoside) containing 50% by weight $C_{12/14}$ alkyl polyglucoside were introduced into a stirred vessel and heated under nitrogen to 80° C. After reaching the temperature, 96.0 kg (2.4 mol) of NaOH prills were added and the mixture was stirred for one hour, its temperature increasing slightly to 105° C. 279.6 g (2.4 mol) of sodium chloroacetate (MCA) were then added and the mixture was stirred at 90° C. until the MCA used had been completely reacted. The reaction was monitored through the quantity of NaCl released. After a reaction time of 3 hours, the reaction was terminated. A viscous, light yellow liquid with the following composition was obtained:

| | |
|---|---|
| free, unreacted APG: | 15.8% |
| NaCl: | 13.5% |
| glycolic acid: | 5.7% |
| Dry residue: | 67.9% |
| $C_{12/14}$ alkyl polyglucoside methyl carboxylate: | 28.9% |

The invention claimed is:

1. A process for the production of an aqueous surfactant mixture comprised of an alkyl and/or alkenyl oligoglycoside ether carboxylic acid comprising reacting in an aqueous solution, in the absence of an organic solvent, an alkyl and/or alkenyl oligoglycoside and an ω-halocarboxylic acid or a salt or ester thereof in the presence of alkali to form an aqueous surfactant mixture comprised of an alkyl and/or alkenyl oligoglycoside ether carboxylic acid.

2. The process of claim 1 wherein the alkyl and/or alkenyl oligoglycoside is a compound of the formula (I):

$$R^1O[G]_p \quad\quad\quad (I)$$

wherein $R^1$ is an alkyl and/or alkenyl group having from 4 to 22 carbon atoms, G is a sugar unit having 5 or 6 carbon atoms and p is a number of from 1 to 10.

3. The process of claim 1 wherein the ω-halocarboxylic acid salt is sodium monochloroacetate.

4. The process of claim 1 wherein the molar ratio of alkyl and/or alkenyl oligoglycoside to the ω-halocarboxylic, salt or ester thereof is from 1:0.5 to 1:3.5.

5. The process of claim 4 wherein the molar ratio is from 1:1 to 1:2.

6. The process of claim 4 wherein the molar ratio is from 1:0.5 to 1:1.5.

7. The process of claim 4 wherein the molar ratio is from 1:1 to 1:1.3.

8. The process of claim 1 wherein the process is carried out at a temperature of from 50 to 100° C.

9. The process of claim 1 wherein water is the only reaction solvent.

10. The process of claim 1 wherein the concentration of the alkyl and/or alkenyl oligoglycoside in the aqueous solution is up to 70% by weight.

11. The process of claim 1 further comprising the step of removing an amount of water such that the residual water content is 5% or less by weight.

* * * * *